(12) United States Patent
Yang et al.

(10) Patent No.: US 11,485,955 B2
(45) Date of Patent: Nov. 1, 2022

(54) FORMULA OF SERUM-FREE MEDIUM FOR HUMAN PLURIPOTENT STEM CELLS

(71) Applicant: Tao Yang, Shanghai (CN)

(72) Inventors: Tao Yang, Shanghai (CN); Yi Sui, Shanghai (CN)

(73) Assignee: Tao Yang, Shanghai (CN)

( * ) Notice: Subject to any disclaimer, the term of this patent is extended or adjusted under 35 U.S.C. 154(b) by 435 days.

(21) Appl. No.: 16/613,475

(22) PCT Filed: Mar. 28, 2017

(86) PCT No.: PCT/CN2017/078390
§ 371 (c)(1),
(2) Date: Nov. 14, 2019

(87) PCT Pub. No.: WO2018/165997
PCT Pub. Date: Sep. 20, 2018

(65) Prior Publication Data
US 2021/0087536 A1 Mar. 25, 2021

(30) Foreign Application Priority Data
Mar. 16, 2017 (CN) .......................... 201710155436.1

(51) Int. Cl.
*C12N 5/074* (2010.01)

(52) U.S. Cl.
CPC ........ *C12N 5/0696* (2013.01); *C12N 2500/14* (2013.01); *C12N 2500/16* (2013.01); *C12N 2500/22* (2013.01); *C12N 2500/24* (2013.01); *C12N 2500/25* (2013.01); *C12N 2500/32* (2013.01); *C12N 2500/34* (2013.01); *C12N 2500/35* (2013.01); *C12N 2500/36* (2013.01); *C12N 2500/38* (2013.01); *C12N 2500/60* (2013.01); *C12N 2500/90* (2013.01); *C12N 2501/11* (2013.01); *C12N 2501/115* (2013.01); *C12N 2501/30* (2013.01)

(58) Field of Classification Search
CPC ............ C12N 2500/14; C12N 2500/16; C12N 2500/22; C12N 2500/24; C12N 2500/32; C12N 2500/34; C12N 2500/35; C12N 2500/36; C12N 2500/38; C12N 2500/60; C12N 2500/90
See application file for complete search history.

(56) References Cited

U.S. PATENT DOCUMENTS

| | | | |
|---|---|---|---|
| 2010/0189699 A1 | 7/2010 | Hattori et al. | |
| 2012/0034674 A1* | 2/2012 | Grillberger | C12P 21/00 435/226 |
| 2014/0170748 A1* | 6/2014 | Bhatia | C12N 5/0665 435/406 |
| 2016/0122718 A1 | 5/2016 | Braam | |

FOREIGN PATENT DOCUMENTS

| | | |
|---|---|---|
| CN | 101711277 A | 5/2010 |
| CN | 102604891 A | 7/2012 |
| CN | 102791278 A | 11/2012 |
| CN | 103555659 A | 2/2014 |
| CN | 103555660 A | 2/2014 |
| CN | 105473708 A | 4/2016 |
| CN | 106957815 A | 7/2017 |
| WO | WO-2011105658 A1 | 9/2011 |

OTHER PUBLICATIONS

R. Ian Freshney, "Defined Media and Supplements." In: Culture of Animal Cell: A Manual of Basic Technique and Specialized Applications. (Hoboken, NJ, John Wiley & Sons, Inc., 2010), pp. 99-114. QH585.2.F74 2010. (Year: 2010).*
International Search Report issued in PCT/CN2017/078390, dated Nov. 17, 2017; ISA/CN.
International Preliminary Report on Patentability (in English and Chinese) issued in PCT/CN2017/078390, dated Sep. 17, 2019.

* cited by examiner

*Primary Examiner* — Kara D Johnson
(74) *Attorney, Agent, or Firm* — Harness, Dickey & Pierce, P.L.C.

(57) ABSTRACT

The present invention discloses formulation of a serum-free medium used for human pluripotent stem cells, which comprises the following raw materials: inorganic salt components, organic components, amino acids and amino acid salts, energy substances and metabolic intermediates, vitamins and antioxidants, proteins and polypeptides, trace elements and chromogenic substances; while the culture process comprises the following steps: selecting a basic formulation, performing combination screening, identifying and evaluating results, and testing a new formulation of culture; and proportioning according to the following methods: adding aforesaid raw materials into 950 ml of water for injection, stirring gently until dissolved, and finally adding 2.438 g of sodium bicarbonate, and stirring gently until dissolved, and then adding 1 liter of water for injection, adjusting the pH to the desired value with 1 mol/L sodium hydroxide solution or 1 mol/L hydrochloric acid solution, finally filtering sterilized with 0.1 μm diameter filter under positive pressure, and storing the medium solution in dark place at 2° C.-8° C., the invention solves the problem of high cost of domestic import of serum-free formulation.

18 Claims, 3 Drawing Sheets

FORMULA OF SERUM-FREE MEDIUM FOR HUMAN PLURIPOTENT STEM CELLS

CROSS-REFERENCE TO RELATED APPLICATIONS

This application is a 371 National Phase of International Application No. PCT/CN2017/078390, filed Mar. 28, 2017, which claims the benefit of Chinese Patent Application No. 201710155436.1 filed on Mar. 16, 2017. The entire disclosures of the above applications are incorporated herein by reference.

FIELD OF INVENTION

The present invention relates to the field of biopharmaceuticals, in particular to the formulation of a serum-free medium used for human pluripotent stem cells.

PRIOR ARTS

Biopharmaceutical is one of the key national development projects. Uniquely, biopharmaceuticals can only be expressed in an active vector such as cell. Traditional chemical synthesis cannot be used for the production of biopharmaceuticals and vaccine. As a necessary raw material of biopharmaceuticals, cell culture medium's grade and enlargement capability of its production scale directly reflect the development level of national biopharmaceutical industry and the cost of drugs. At present, the development and production technology of high-quality serum-free medium and the global market of cell culture medium are generally monopolized by American companies such as Sigma, Life and HYCLONE, therefore, the delivery time and cost are limited by these companies, which is one of the key factors that hinder the domestic enterprises' large-scale industrialization and competition with the international biopharmaceutical companies with low costs. The Chinese Pharmacopoeia 2010 and GMP regulations put forward higher requirements on the cell culture medium used by domestic biopharmaceutical companies. Serum-free medium is a necessary condition for approval of new drugs, although serum-supplemented medium is still allowed to be used by some approved old products. However, due to the lack of high-quality, industrialized serum-free cell culture medium in China, high-quality of serum-free cell culture medium used by domestic enterprises still generally relies on imports. The serum-free cell culture medium developed by the present invention is in the international advanced level and will fill the gap of high-end products of domestic serum-free cell culture medium.

Due to the shortage in human resource of R & D technicians and production technology of industrialization, the R & D and production technology of serum-free cell culture medium in China is still unsophisticated. According to the data released in April 2008 by Beijing Tsinghua Skywing Technology Co., Ltd., a cell-culture medium supplying domestic company acquired by Merck, serum-free medium from Skywing can sustain antibody production of approximately 300 mg/L, which is 10 times less than the average antibody yield of 2-3 g/L currently supported by foreign culture medium. It means that biopharmaceuticals sustained by cell-culture medium from the present largest domestic company shall cost 10 times more than biopharmaceuticals supported by cell-culture medium from foreign companies to achieve the same profitability. While its formulation is publicly available and the products should be used with serum, low-end commercial products applying on the approved old vaccine is produced by another domestic company in the market, having an annual production of less than 30 tons. All of the high value-added serum-free cell culture medium used for the rest of biosimilars and high-end vaccines rely on imports. Therefore, it is necessary to develop our own large-scale industrial culture technologies for serum-free cells.

CONTENT OF THE PRESENT INVENTION

The purpose of present invention is to provide a formulation of the serum-free medium for human pluripotent stem cells, wherein the serum-free medium product is in an international advanced level, and the gap of high-end products of domestic serum-free cell culture medium will be filled and the problems raised in prior arts will be solved.

To achieve the purpose described above, the present invention provides the following technical solution: a formulation of serum-free medium for human pluripotent stem cells, which includes the following raw materials: inorganic salt components, organic components, amino acids and amino acid salts, energy substances and metabolic intermediates, vitamins and antioxidants, proteins and polypeptides, trace elements and chromogenic substances; while the culture process includes the following steps: selecting a basic formulation, performing combination screening, identifying and evaluating results, and testing a new formulation of culture; and proportioning according to the following methods:

S1: adding aforesaid raw materials into 950 ml of water for injection at 20° C.-30° C., and stirring gently until dissolved;

S2: adding 2.438 g of sodium bicarbonate, and stirring gently until dissolved, and then adding 1 liter of water for injection;

S3: adjusting the pH to the desired value with 1 mol/L sodium hydroxide solution or 1 mol/L hydrochloric acid solution;

S4: filtering sterilized with 0.1 μm diameter filter under positive pressure, and storing the medium solution in dark place at 2° C.-8° C.

Preferably, the specific weight ratio of the inorganic salt components includes: 116.6 mg of anhydrous calcium chloride, 311.8 mg of potassium chloride, 28.64 mg of magnesium chloride, 48.84 mg of anhydrous magnesium sulfate, 6999.5 mg of sodium chloride, 54.35 mg of anhydrous sodium dihydrogen phosphate and 71.02 mg of disodium hydrogen phosphate.

Preferably, the specific weight ratio of the organic components includes: 0.081 mg of 4-butanediamine dihydrochloride, 55 mg of sodium pyruvate, 2 mg of pyridoxal hydrochloride, and 0.031 mg of pyridoxine hydrochloride.

Preferably, the specific weight ratio of the amino acids and amino acid salts includes: 59.05 mg of L-leucine, 91.25 mg of L-lysine hydrochloride, 17.24 mg of L-methionine, 35.48 mg of L-phenylalanine, 26.25 mg of L-serine, 53.45 mg of L-threonine, 4.45 mg of L-alanine, 7.5 mg of L-asparagine, 6.65 mg of L-aspartic acid, 26.34 mg of L-cysteine hydrochloride, 11.03 mg of L-glutamic acid, 147.5 mg of L-arginine hydrochloride, 17.25 mg of L-proline, 31.29 mg of L-cystine hydrochloride, 9.02 mg of L-tryptophan, 365 mg of L-glutamine, 38.4 mg of L-tyrosine, 28.13 mg of glycine, 52.85 mg of L-valine, 31.48 mg of L-histidine hydrochloride, 54.47 mg of L-isoleucine and 6.82 mg of L-hydroxyproline.

Preferably, the specific weight ratio of the energy substances and metabolic intermediates added includes: 0.042 mg of linoleic acid, 12.6 mg of inositol, 8.98 mg of choline chloride, 2.02 mg of nicotinamide, 3151 mg of D-glucose, 0.365 mg of thymidine and 2 mg of hypoxanthine.

Preferably, the specific weight ratio of the vitamins and antioxidants includes: 0.105 mg of lipoic acid, 0.0035 mg of vitamin H, 2.24 mg of D-calcium pantothenate, 2.65 mg of folic acid, 0.219 mg of riboflavin, 2.17 mg of thiamine hydrochloride, 0.4 mg of vitamin B2, 0.68 mg of vitamin B12, 87.54 mg of vitamin C-2-phosphate.

Preferably, the specific weight ratio of the proteins and polypeptides includes: 4000 mg of transferrin, 1200 mg of insulin, 2.0 mg of basic fibroblast growth factor, 1.65 mg of epidermal growth factor, 856.36 mg of human serum albumin, 150 mg of progesterone.

Preferably, the specific weight ratio of the trace elements includes: 0.0013 mg of copper sulfate pentahydrate, 0.05 mg of iron nitrate nonahydrate, 0.417 mg of ferrous sulfate heptahydrate, 0.432 mg of zinc sulfate heptahydrate, 0.0085 mg of silver fluoride dihydrate, 0.049 mg of aluminum sulfate octadecahydrate, 0.0092 mg of barium chloride dihydrate, 0.0008 mg of cadmium sulfate octahydrate, 0.0057 mg of cobalt sulfate heptahydrate, 0.0038 mg of chromium nitrate nonahydrate, 0.0009 mg of sodium metagermanate hydrate, 0.013 mg of sodium selenite pentahydrate, 0.0071 mg of potassium bromide, 0.0007 mg of sodium iodide dihydrate, 0.0025 mg of manganese sulfate heptahydrate, 0.034 mg of sodium silicate nonahydrate, 0.06 mg of sodium metavanadate dihydrate, 0.074 mg of sodium molybdate dehydrate, 0.0086 mg of nickel chloride hexahydrate, 0.0017 mg of rubidium chloride, 0.0054 mg of potassium stannate trihydrate, 0.004 mg of zirconyl nitrate dihydrate.

Preferably, the chromogenic substance is 8.1 mg of phenol red.

Preferably, the properties of the medium solution in S4 are solubility, completely dissolved and clear.

Preferably, the adjustment of pH value in S3: pH 6.60-7.20 with addition of $NaHCO_3$, or pH 5.50-6.10 without addition of $NaHCO_3$; the osmotic pressure (mOsm/kgH$_2$O) is: 277-312 with addition of $NaHCO_3$ and 234-258 without addition of $NaHCO_3$; the concentration of bacterial endotoxin ≤10 EU/ml; the microbial biomass in microbiological examination ≤1000 CFU/g.

Compared with the prior arts, the beneficial effects of the present invention are as follows:

The formulation of serum-free medium for human pluripotent stem cells has the advantages of large market and wide applications, wherein the product of serum-free medium is in an international advanced level, and the gap of high-end products of domestic serum-free cell culture medium will be filled. Serum-free cell culture medium is needed by the production of all cell-based vaccine and macromolecular biopharmaceuticals (including monoclonal antibodies and recombinant protein drugs). The invention solves the problem of high cost of domestic importing serum-free formulation.

DETAILED DESCRIPTION OF THE PREFERRED EMBODIMENT

Hereinafter, the technical solutions in the embodiments of the present invention will be described clearly and completely with reference to the accompanying drawings in the embodiments of the present invention. Apparently, the described embodiments are merely part of, and not all embodiments, of the present invention. Based on the embodiments of the present invention, all other embodiments obtained by a person of ordinary skill in the art without performing creative efforts shall fall within the protection scope of the present invention.

Figure 1:
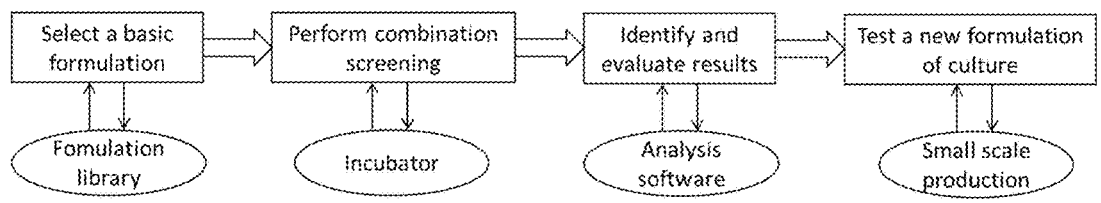
FIG. 1 is an overall flow chart of the present invention.

Referring to FIG. 1, the present invention provides a technical solution: a formulation of serum-free medium for human pluripotent stem cells, which includes the following raw materials: inorganic salt components, organic components, amino acids and amino acid salts, energy substances and metabolic intermediates, vitamins and antioxidants, proteins and polypeptides, trace elements and chromogenic substances; in which the specific weight ratio of the inorganic salt components includes: 116.6 mg of anhydrous calcium chloride, 311.8 mg of potassium chloride, 28.64 mg of magnesium chloride, 48.84 mg of anhydrous magnesium sulfate, 6999.5 mg of sodium chloride, 54.35 mg of anhydrous sodium dihydrogen phosphate and 71.02 mg of disodium hydrogen phosphate; the specific weight ratio of the organic components includes: 0.081 mg of 4-butanediamine dihydrochloride, 55 mg of sodium pyruvate, 2 mg of pyridoxal hydrochloride, and 0.031 mg of pyridoxine hydrochloride; the specific weight ratio of the amino acids and amino acid salts includes: 59.05 mg of L-leucine, 91.25 mg of L-lysine hydrochloride, 17.24 mg of L-methionine, 35.48 mg of L-phenylalanine, 26.25 mg of L-serine, 53.45 mg of L-threonine, 4.45 mg of L-alanine, 7.5 mg of L-asparagine, 6.65 mg of L-aspartic acid, 26.34 mg of L-cysteine hydrochloride, 11.03 mg of L-glutamic acid, 147.5 mg of L-arginine hydrochloride, 17.25 mg of L-proline, 31.29 mg of L-cystine hydrochloride, 9.02 mg of L-tryptophan, 365 mg of L-glutamine, 38.4 mg of L-tyrosine, 28.13 mg of glycine, 52.85 mg of L-valine, 31.48 mg of L-histidine hydrochloride, 54.47 mg of L-isoleucine and 6.82 mg of L-hydroxyproline; the specific weight ratio of the energy substances and metabolic intermediates added includes: 0.042 mg of linoleic acid, 12.6 mg of inositol, 8.98 mg of choline chloride, 2.02 mg of nicotinamide, 3151 mg of D-glucose, 0.365 mg of thymidine and 2 mg of hypoxanthine; the specific weight ratio of the vitamins and antioxidants includes: 0.105 mg of lipoic acid, 0.0035 mg of vitamin H, 2.24 mg of D-calcium pantothenate, 2.65 mg of folic acid, 0.219 mg of riboflavin, 2.17 mg of thiamine hydrochloride, 0.4 mg of vitamin B2, 0.68 mg of vitamin B12, 87.54 mg of vitamin C-2-phosphate; the specific weight ratio of the proteins and polypeptides includes: 4000 mg of transferrin, 1200 mg of insulin, 2.0 mg of basic fibroblast growth factor, 1.65 mg of epidermal growth factor, 856.36 mg of human serum albumin, 150 mg of progesterone; the specific weight ratio of the trace elements includes: 0.0013 mg of copper sulfate pentahydrate, 0.05 mg of iron nitrate nonahydrate, 0.417 mg of ferrous sulfate heptahydrate, 0.432 mg of zinc sulfate heptahydrate, 0.0085 mg of silver fluoride dihydrate, 0.049 mg of aluminum sulfate octadecahydrate, 0.0092 mg of barium chloride dihydrate, 0.0008 mg of cadmium sulfate octahydrate, 0.0057 mg of cobalt sulfate heptahydrate, 0.0038 mg of chromium nitrate nonahydrate, 0.0009 mg of sodium metagermanate hydrate, 0.013 mg of sodium selenite pentahydrate, 0.0071 mg of potassium bromide, 0.0007 mg of sodium iodide dihydrate, 0.0025 mg of manganese sulfate heptahydrate, 0.034 mg of sodium silicate nonahydrate, 0.06 mg of sodium metavanadate dihydrate, 0.074 mg of sodium molybdate dehydrate, 0.0086 mg of nickel chloride hexahydrate, 0.0017 mg of rubidium chloride, 0.0054 mg of potassium stannate trihydrate, 0.004 mg of zirconyl nitrate dehydrate; the chromogenic substance is 8.1 mg of phenol red.

The culture process includes the following steps: selecting a basic formulation, performing combination screening, identifying and evaluating results, testing a new formulation of culture; and proportioning according to the following methods:

Step 1: adding aforesaid raw materials into 950 ml of water for injection at 20° C.-30° C., and stirring gently until dissolved;

Step 2: adding 2.438 g of sodium bicarbonate, and stirring gently until dissolved, and then adding 1 liter of water for injection;

Step 3: adjusting the pH to the desired value with 1 mol/L sodium hydroxide solution or 1 mol/L hydrochloric acid solution; the adjustment of pH value is that pH 6.60-7.20 with addition of $NaHCO_3$, pH 5.50-6.10 without addition of $NaHCO_3$; the osmotic pressure (mOsm/kg$H_2O$) is: 277-312 with addition of $NaHCO_3$ and 234-258 without addition of $NaHCO_3$; the concentration of bacterial endotoxin ≤10 EU/ml; the microbial biomass in microbiological examination ≤1000 CFU/g.

Step 4: filtered-sterilizing with 0.1 μm diameter filter membrane under positive pressure, and storing the medium solution in dark place at 2° C.-8° C.; the properties of the medium solution in S4 are solubility, completely dissolved and clear.

Embodiment 1

Figure 6:
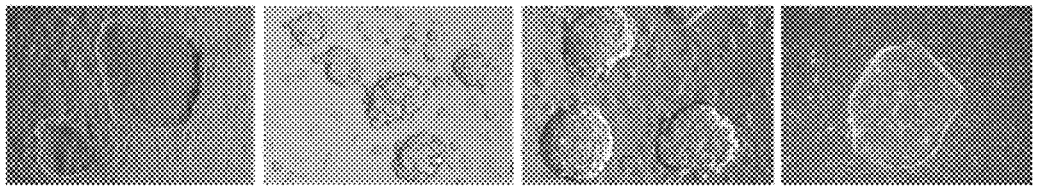
FIG. 6 is an efficiency comparison of the culture expansion of pluripotent stem cells in different media.
Figure 7:
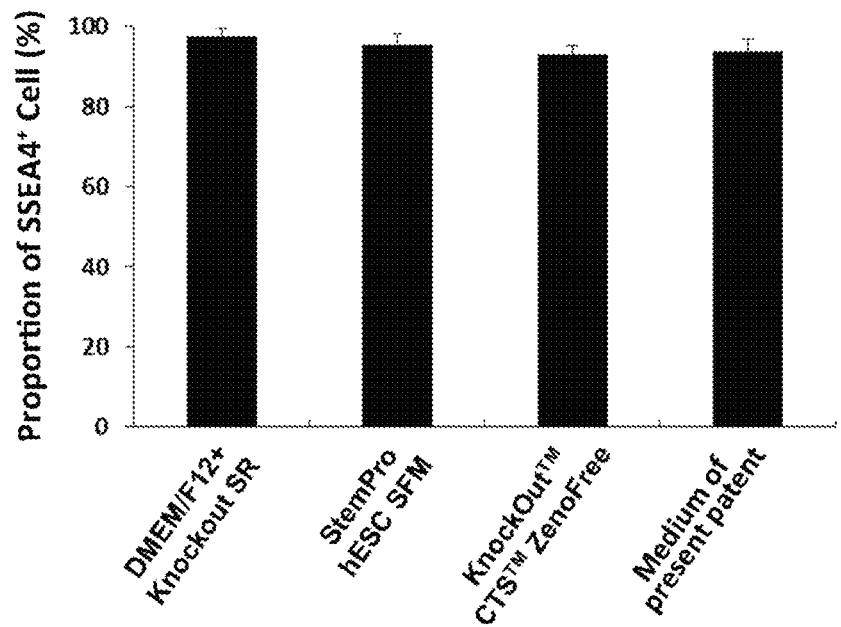
FIG. 7 is a comparison of SSEA-4$^+$ proportions in cells in culture expansion using different media.

Referring to FIG. 6-7, a formulation of serum-free medium for human pluripotent stem cells includes the following raw materials: inorganic salt components, organic components, amino acids and amino acid salts, energy substances and metabolic intermediates, vitamins and antioxidants, proteins and polypeptides, trace elements and chromogenic substances; human pluripotent stem cells are expanded and cultured according to the method described above.

Culture expansion of human pluripotent stem cells: newly prepared bFGF (i.e., basic fibroblast growth factor, 2 mg of bFGF per liter of culture medium) and β-mercaptoethanol (7 μl of β-mercaptoethanol per liter of culture medium) are pipetted into the prepared culture medium; the undifferentiated state of human pluripotent stem cells are maintained, the pluripotent stem cells are expanded and cultured so that the pluripotent stem cells are able to self-renew and proliferate to achieve the purpose of increasing the number of cells, expanding the storage, subsequently sub-packing and preserving cells; compared with similar products (DMEM/F12+Knockout SR (Invitrogen), StemPro hESC SFM, KnockOut™ CTS™ ZenoFree medium) in the current market, there is no difference in cell colony morphology while culturing h-14 (Wicell Research Institute, Madison, Wis., USA), a human embryonic stem cell line; a specific protein is expressed by human pluripotent stem cells in undifferentiated state, namely SSEA-4 (stage specific embryonic antigen-4), and there is no significant difference in the proportion of SSEA-4 positive cells between the culture medium from present formulation and similar products in the market.

Embodiment 2

Figure 2:
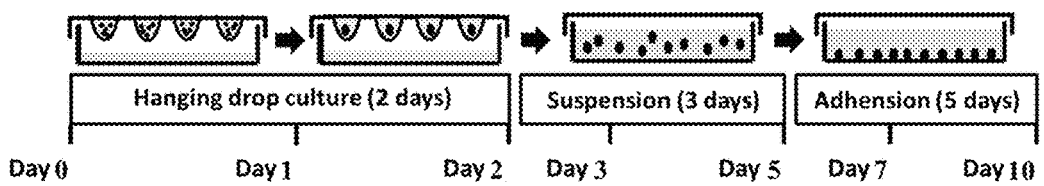
FIG. 2 is the time-course plots of directional induction and culture of cardiomyocytes from pluripotent stem cells.
Figure 3:
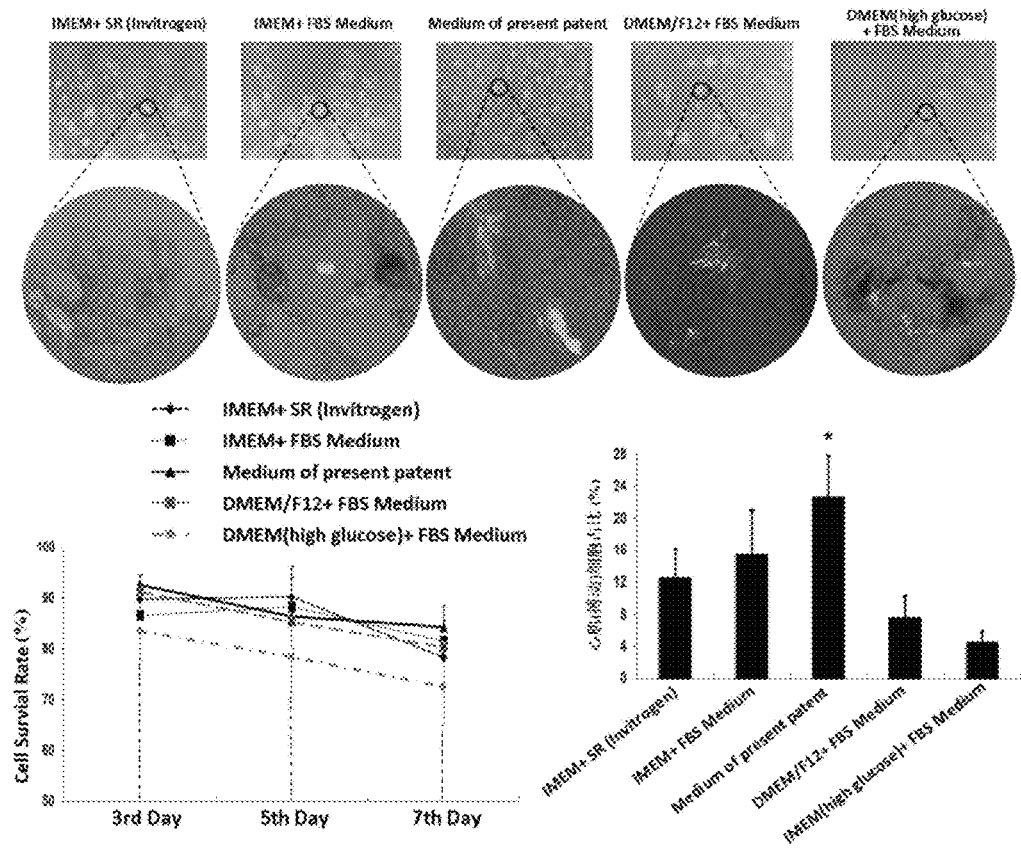
FIG. 3 is the compared pattern diagram of directional induction and culture of cardiomyocytes from human pluripotent stem cells using different media.

Referring to FIG. 2-3, a formulation of serum-free medium for human pluripotent stem cells includes the following raw materials: inorganic salt components, organic components, amino acids and amino acid salts, energy substances and metabolic intermediates, vitamins and antioxidants, proteins and polypeptides, trace elements and chromogenic substances; cardiomyocytes are induced and cultured according to the above-mentioned method, the culture process includes the following steps: hanging-drop culturing for 3 days+suspension culturing for 2 days+adherent culturing for 5 days with the addition of vitamin C (128.05 mg of ascorbic acid per liter of culture medium is added).

Induction and culture of cardiomyocytes: human pluripotent stem cell line IMR90-1 (Wicell Research Institute, Madison, Wis., USA) is used; the reporter gene MHC-eGFP (myosin heavy chain promoter-driven enhanced green fluorescent protein is expressed by means of electric transfection, green fluorescent signal appeared once the stem cells are differentiated to cardiomyocytes and the cardiomyocyte-specific MHC is expressed after cell induction and culture) is transfected into IMR90-1 by electrotransfection before induction and culture, and then induces and cultures the cell line with different induction and culture systems (including IMEM+15% SR (Invitrogen), IMEM+15% fetal bovine serum, medium by the present formulation (no serum), DMEM/F12+15% fetal bovine serum, DMEM (high glucose)+15% fetal bovine serum, respectively), samples have been taken at different time points according to the schedule shown in FIG. 2 in order to compare the efficiency of induction using different media; the comparison results shows that culture medium of the present formulation is superior to similar products currently on the market (*$p<0.05$ difference is significant compared with any other products) based on the evaluation index of cell survival rates on the 3rd, 5th, 7th day and the proportion of cardiomyocytes generated on 7th day (FIG. 3).

Embodiment 3

Figure 4:
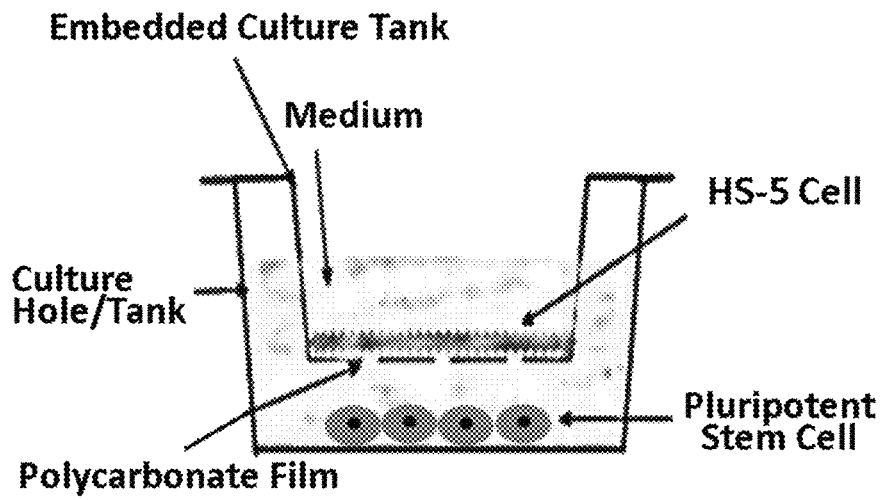
FIG. 4 is a pattern diagram of directional induction and culture of neural cells from human pluripotent stem cells.
Figure 5:
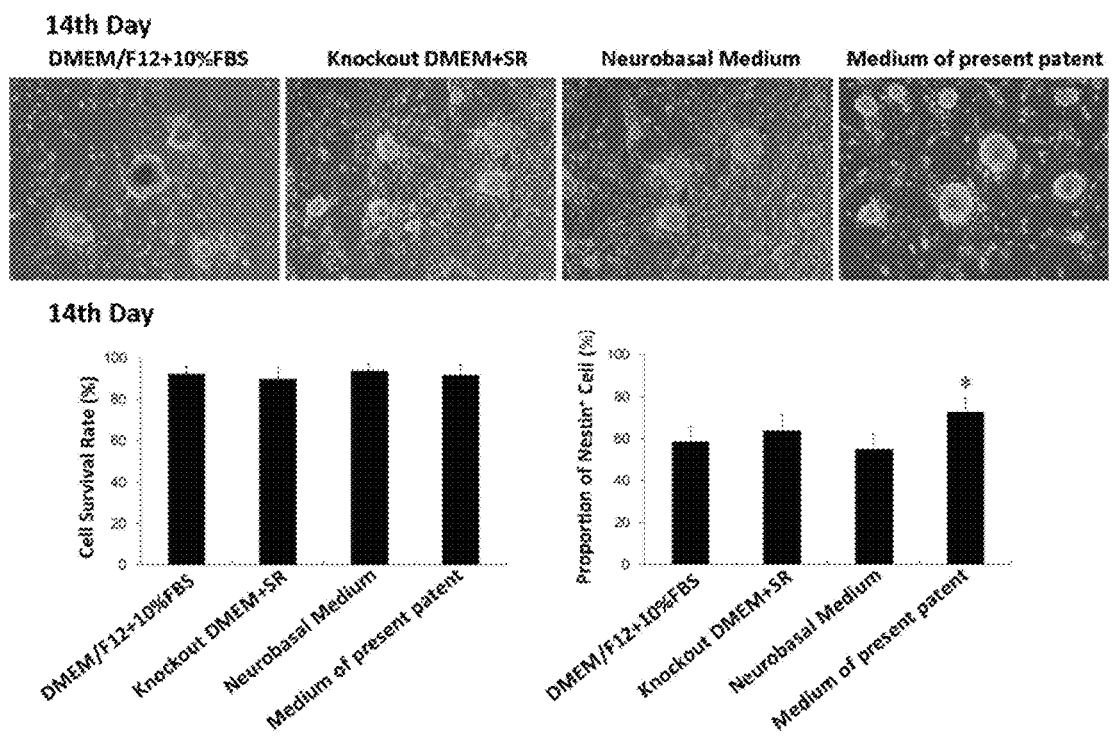
FIG. 5 is an efficiency comparison of directional induction and culture of neural cells from human pluripotent stem cells using different media.

Referring to FIG. 4-5, a formulation of serum-free medium for human pluripotent stem cells includes the following raw materials: inorganic salt components, organic components, amino acids and amino acid salts, energy substances and metabolic intermediates, vitamins and antioxidants, proteins and polypeptides, trace elements and chromogenic substances; neural cells are induced according to the method described above: HS-5 cell line is used as a feeder layer in the prepared culture medium and NT-3 (1342 mg of NT-3 (i.e., neurotrophin-3) per liter of culture medium) is added at the same time.

Induction and culture of neural cells: human pluripotent stem cell line iPS-1 (Wicell Research Institute, Madison, Wis., USA) is used to co-culture with human bone marrow stromal cell line HS-5 in order to induce and culture neural cells from pluripotent stem cells; the similar products to be compared in current market includes DMEM/F12+10% fetal bovine serum, Knockout DMEM+10% SR (Invitrogen) and Neurobasal medium; after 2 weeks of inducing and culturing according to the method of FIG. 4, the cell survival rate and proportion of Nestin$^+$ cells (Nestin is a cell surface marker specifically expressed by neural progenitor cells) are used as evaluation index to compare the efficiency of different media on neural induction of pluripotent stem cells; the comparison results showed that there is no significant difference in cell survival rate between different media, but medium prepared by the present formulation is superior to similar products on the current market in terms of the proportion of Nestin$^+$ cells (FIG. 5; *p<0.05 difference is significant compared with any other products).

In conclusion, the formulation of the serum-free medium for human pluripotent stem cells has the advantages of large market and wide applications, wherein the serum-free medium product is in an international advanced level, and the gap of high-end products of domestic serum-free cell culture medium will be filled. Serum-free cell culture medium is needed by the production of all cell-based vaccine and macromolecular biopharmaceuticals (including monoclonal antibodies and recombinant protein drugs). The invention solves the problem of high cost of domestic import of serum-free formulation.

While specific embodiments of the present invention have been described above, it will be understood by those of skilled in the art that these embodiments are merely illustrative and that various changes and modifications may be made to these embodiments without departing from the principles and spirit of the present invention. Therefore, the protection scope of the present invention is defined by the appended claims.

What is claimed is:

1. A formulation of a serum-free medium for human pluripotent stem cells, comprising the following raw materials: inorganic salt components, organic components, amino acids and amino acid salts, energy substances and metabolic intermediates, vitamins and antioxidants, proteins and polypeptides, and trace elements and chromogenic substances,
    wherein the specific weight ratio of said amino acids and amino acid salts comprises: 59.05 mg of L-leucine, 91.25 mg of L-lysine hydrochloride, 17.24 mg of L-methionine, 35.48 mg of L-phenylalanine, 26.25 mg of L-serine, 53.45 mg of L-threonine, 4.45 mg of L-alanine, 7.5 mg of L-asparagine, 6.65 mg of L-aspartic acid, 26.34 mg of L-cysteine hydrochloride, 11.03 mg of L-glutamic acid, 147.5 mg of L-arginine hydrochloride, 17.25 mg of L-proline, 31.29 mg of L-cystine hydrochloride, 9.02 mg of L-tryptophan, 365 mg of L-glutamine, 38.4 mg of L-tyrosine, 28.13 mg of glycine, 52.85 mg of L-valine, 31.48 mg of L-histidine hydrochloride, 54.47 mg of L-isoleucine and 6.82 mg of L-hydroxyproline.

2. The formulation of a serum-free medium for human pluripotent stem cells according to claim 1, wherein the specific weight ratio of said inorganic salt components comprises: 116.6 mg of anhydrous calcium chloride, 311.8 mg of potassium chloride, 28.64 mg of magnesium chloride, 48.84 mg of anhydrous magnesium sulfate, 6999.5 mg of sodium chloride, 54.35 mg of anhydrous sodium dihydrogen phosphate and 71.02 mg of disodium hydrogen phosphate.

3. The formulation of a serum-free medium for human pluripotent stem cells according to claim 1, wherein the specific weight ratio of said organic components comprises: 0.081 mg of 1,4-butanediamine dihydrochloride, 55 mg of sodium pyruvate, 2 mg of pyridoxal hydrochloride, and 0.031 mg of pyridoxine hydrochloride.

4. The formulation of a serum-free medium for human pluripotent stem cells according to claim 1, wherein the specific weight ratio of said energy substances and metabolic intermediates added comprises: 0.042 mg of linoleic acid, 12.6 mg of inositol, 8.98 mg of choline chloride, 2.02 mg of nicotinamide, 3151 mg of D-glucose, 0.365 mg of thymidine and 2 mg of hypoxanthine.

5. The formulation of a serum-free medium for human pluripotent stem cells according to claim 1, wherein the specific weight ratio of said vitamins and antioxidants comprises: 0.105 mg of lipoic acid, 0.0035 mg of vitamin H, 2.24 mg of D-calcium pantothenate, 2.65 mg of folic acid, 0.219 mg of riboflavin, 2.17 mg of thiamine hydrochloride, 0.4 mg of vitamin B2, 0.68 mg of vitamin B12, 87.54 mg of vitamin C-2-phosphate.

6. The formulation of a serum-free medium for human pluripotent stem cells according to claim 1, wherein the specific weight ratio of said proteins and polypeptides comprises: 4000 mg of transferrin, 1200 mg of insulin, 2.0 mg of basic fibroblast growth factor, 1.65 mg of epidermal growth factor, 856.36 mg of human serum albumin, 150 mg of progesterone.

7. The formulation of a serum-free medium for human pluripotent stem cells according to claim 1, wherein the specific weight ratio of said trace elements comprises: 0.0013 mg of copper sulfate pentahydrate, 0.05 mg of iron nitrate nonahydrate, 0.417 mg of ferrous sulfate heptahydrate, 0.432 mg of zinc sulfate heptahydrate, 0.0085 mg of silver fluoride dihydrate, 0.049 mg of aluminum sulfate octadecahydrate, 0.0092 mg of barium chloride dihydrate, 0.0008 mg of cadmium sulfate octahydrate, 0.0057 mg of cobalt sulfate heptahydrate, 0.0038 mg of chromium nitrate nonahydrate, 0.0009 mg of sodium metagermanate hydrate, 0.013 mg of sodium selenite pentahydrate, 0.0071 mg of potassium bromide, 0.0007 mg of sodium iodide dihydrate, 0.0025 mg of manganese sulfate heptahydrate, 0.034 mg of sodium silicate nonahydrate, 0.06 mg of sodium metavanadate dihydrate, 0.074 mg of sodium molybdate dehydrate, 0.0086 mg of nickel chloride hexahydrate, 0.0017 mg of rubidium chloride, 0.0054 mg of potassium stannate trihydrate, 0.004 mg of zirconyl nitrate dihydrate.

8. The formulation of a serum-free medium for human pluripotent stem cells according to claim 1, wherein said chromogenic substance is 8.1 mg of phenol red.

9. The formulation of a serum-free medium for human pluripotent stem cells according to claim 1, wherein the serum-free medium includes at least one of a pH value in the range of 6.60-7.20 and an osmotic pressure in the range of 277-312 mOsm/kgH$_2$O.

10. A method for preparing the serum-free medium, comprising the following steps:
    S1: adding the raw materials described in claim 1 into 950 ml of water for injection at 20° C.-30° C., and stirring gently until dissolved;
    S2: adding 2.438 g of sodium bicarbonate, and stirring gently until dissolved, and then adding 1 liter of water for injection;
    S3: adjusting the pH to the desired value with 1 mol/L sodium hydroxide solution or 1 mol/L hydrochloric acid solution.

11. The method of claim 10, further comprising:
    S4: filtering sterilized with 0.1 μm diameter filter under positive pressure, and storing the medium solution in dark place at 2° C.-8° C.

12. The method of claim 10, wherein, regarding the adjustment of pH value in S3: the pH value is 6.60-7.20; and/or, the osmotic pressure of the serum-free medium is 277-312 mOsm/kgH$_2$O.

13. A method for cultivating human pluripotent stem cells, wherein, the human pluripotent stem cells are cultivated in the serum-free medium of claim 1.

14. The method of claim 13, further comprising adding freshly prepared bFGF and β-mercaptoethanol to the serum-free medium.

15. The method of claim 14, wherein, the concentration of bFGF and β-mercaptoethanol are 2 mg/L and 7 µl/L, respectively.

16. The method of claim 13, wherein, the human pluripotent stem cells are human pluripotent stem cell line IMR90-1 or iPS-1.

17. The method of claim 16, wherein, a reporter gene, MHC-eGFP, was transfected into IMR90-1 by electrotransfection before induction and cultivation.

18. The method of claim 16, wherein, the iPS-1 was co-cultured with human bone marrow stromal cell line HS-5.

\* \* \* \* \*